US010314613B2

(12) United States Patent
Ollivier et al.

(10) Patent No.: US 10,314,613 B2
(45) Date of Patent: Jun. 11, 2019

(54) EXPLANTATION ACCESSORY FOR AN INTRACORPOREAL CAPSULE

(71) Applicant: SORIN CRM SAS, Clamart (FR)

(72) Inventors: Jean-François Ollivier, Villiers le Bâcle (FR); Nicolas Shan, Juvisy-sur-Orge (FR); Philippe D'hiver, Châtillon (FR)

(73) Assignee: Sorin CRM SAS, Clamart (FR)

( * ) Notice: Subject to any disclaimer, the term of this patent is extended or adjusted under 35 U.S.C. 154(b) by 341 days.

(21) Appl. No.: 14/874,084

(22) Filed: Oct. 2, 2015

(65) Prior Publication Data
US 2016/0095611 A1    Apr. 7, 2016

(30) Foreign Application Priority Data
Oct. 6, 2014    (FR) ...................... 14 59570

(51) Int. Cl.
*A61B 17/34* (2006.01)
*A61N 1/375* (2006.01)
(Continued)

(52) U.S. Cl.
CPC .......... *A61B 17/3468* (2013.01); *A61B 17/50* (2013.01); *A61N 1/362* (2013.01);
(Continued)

(58) Field of Classification Search
CPC .. A61N 1/3756; A61N 1/362; A61N 1/37205; A61N 2001/0578;
(Continued)

(56) References Cited

U.S. PATENT DOCUMENTS 3,903,892 A * 9/1975 Komiya ............. A61B 1/00098
606/110
4,718,419 A * 1/1988 Okada .............. A61B 17/32056
606/39
(Continued)

FOREIGN PATENT DOCUMENTS

WO  WO-2011/057210   5/2011
WO  WO-2012/058067   5/2012
WO  WO-2012/082755   6/2012

OTHER PUBLICATIONS

Preliminary Search Report for French Patent Application No. 1459570, dated Feb. 23, 2015, 1 page.

*Primary Examiner* — David C Eastwood
(74) *Attorney, Agent, or Firm* — Foley & Lardner LLP

(57) ABSTRACT

An explantation accessory includes a catheter with a steerable head carrying a tubular receptacle adapted to accommodate the proximal portion of the capsule. The explantation accessory further includes a lasso having a flexible wire extending along the catheter to and forming at its distal end a deformable loop. One end of the deformable loop is mobile so as to allow tightening of the loop under the effect of a traction exerted on the flexible wire along the catheter. The free end edge of the tubular receptacle comprises a protruding anterior portion, an axially recessed posterior portion with respect to the anterior portion and located diametrically opposite to the protruding anterior portion, and two beveled edges connecting the protruding anterior portion to the recessed posterior portion.

8 Claims, 4 Drawing Sheets

(51) Int. Cl.
*A61B 17/50* (2006.01)
*A61N 1/362* (2006.01)
*A61N 1/372* (2006.01)
A61B 17/22 (2006.01)
A61N 1/05 (2006.01)
A61B 17/00 (2006.01)
A61B 90/00 (2016.01)

(52) U.S. Cl.
CPC ....... *A61N 1/3756* (2013.01); *A61N 1/37205* (2013.01); *A61B 2017/00358* (2013.01); *A61B 2017/22035* (2013.01); *A61B 2090/3966* (2016.02); *A61N 2001/0578* (2013.01)

(58) Field of Classification Search
CPC .......... A61B 17/32056; A61B 17/3468; A61B 2017/347; A61B 17/50; A61B 2017/22035; A61B 2017/00358
See application file for complete search history.

(56) References Cited

U.S. PATENT DOCUMENTS

| | | | | |
|---|---|---|---|---|
| 5,201,741 | A * | 4/1993 | Dulebohn | A61B 17/32056 606/110 |
| 6,068,603 | A * | 5/2000 | Suzuki | A61B 10/04 600/564 |
| 2005/0119524 | A1* | 6/2005 | Sekine | A61B 1/00135 600/114 |
| 2006/0212042 | A1* | 9/2006 | Lamport | A61B 17/221 606/108 |
| 2013/0103047 | A1 | 4/2013 | Steingisser et al. | |

\* cited by examiner

EXPLANTATION ACCESSORY FOR AN INTRACORPOREAL CAPSULE

CROSS-REFERENCE TO RELATED PATENT APPLICATIONS

This application claims the benefit of and priority to French Patent Application No. 1459570, filed Oct. 6, 2014, which is incorporated herein by reference in its entirety.

BACKGROUND

The invention relates to "active implantable medical devices" as defined by the Directive 90/385/EEC of 20 Jun. 1990 of the Council of the European communities, particularly to devices that continuously monitor heart rhythm and deliver if necessary stimulation, resynchronization and/or defibrillation electrical pulses to the heart in case of arrhythmia detected by the device.

The invention relates especially, but is not limited, to those devices which are in the form of an autonomous capsule for implantation in a heart chamber (atrium or ventricle, right or left).

The capsules are free of any mechanical connection to an implantable (such as a housing of the stimulation pulse generator) or non-implantable (external device such as programmer or monitoring device for patient remote monitoring) main device, and for this reason are called "leadless capsules" to distinguish them from electrodes or sensors disposed at the distal end of a conventional probe (lead), which is traversed throughout its length by one or more conductors galvanically connecting the electrode or sensor to a generator connected to an opposite, proximal end of the lead. However the autonomous nature of the capsule is not inherently a necessary feature of the invention.

The invention is applicable to the explantation of such capsules provided at their distal end with an anchoring member such as an helical screw, axially extending from the body of the capsule and designed to penetrate into the cardiac tissue by screwing during implantation at the selected site. The explantation is particularly delicate because it is necessary, first, to catch the body of the capsule via an explantation accessory and, second, to exert on the body a rotation torque to detach it from the implantation site wherein it was maintained by the anchoring screw. This torque should be large enough to overcome resistance and adhesions resulting from fibrous tissue that are locally formed.

Explantation accessories, designated as "lassos" or snares, are commonly used to capture and remove medical equipment such as a lead body, defective catheters, guides, etc., out of the heart chambers and venous system. These lassos consist of a flexible wire terminated at its distal end by a deformable loop of shape memory metal, the loop extending in the free state in a plane generally perpendicular to the metal wire that supports it. The metal wire is introduced into the distal orifice of a catheter, crossing therethrough to emerge proximally. The tension of the wire from the proximal end of the catheter has the effect, at the other end, to draw the loop by making it gradually enter the catheter wherein it will be housed.

The operation consists in introducing the catheter into the patient's body, with the loop fully folded in the distal end region. The loop is then deployed from the catheter by pushing the wire from the proximal end. Due of the shape memory of the metal, the loop then resumes its lasso shape inclined relative to the direction of the wire and of the catheter. The lasso can be oriented at will to capture the element to be extracted. Pulling on the wire then makes it possible to partially enter the loop in the catheter, which has the effect of reducing its size and ensuring clamping of the element to be removed.

WO 2012/082755 A1 describes a leadless capsule explantation accessory based on this principle, which implements a catheter with a lasso mechanism to permit capture of the capsule at the distal end of the catheter, a docking member being possibly coupled to the proximal end of the capsule. When the loop of the lasso is tightened, the catheter docking member is coupled to the capsule, allowing the transmission of an unscrewing and removal torque of the capsule, which remains fixed to the docking member.

The drawback of this type of device is the issue that, when handling the lasso, it could trap valve tissue or filaments present in the vicinity of the capture, especially when tightening the loop lasso. Tissues, and in particular the valve tissues, captured in the same time as the capsule, could be damaged at the time of extraction.

The tissue capture risk is increased by the lack of visibility during the operation, which is performed by a practitioner under an image intensifier coupled with X-ray equipment, remote from the explantation site (typically with a femoral access for introduction of the catheter intended to reach the right ventricular cavity). The risk is increased also by the difficulty in controlling the fixation of the lasso to the capsule before removing the assembly.

SUMMARY

One object of the invention is to provide a sophisticated explantation accessory that prevents the adhesion of valve tissue filaments during the capture of the capsule by the lasso, and the docking of the catheter with the proximal part of the capsule.

To this end, the invention provides an explantation accessory for intracorporeal capsule including, in a manner itself known from WO 2012/082755 A1 cited above, a tubular body provided at its distal end with a screw anchoring member adapted to penetrate into a tissue of a wall of an organ of a patient. The explantation accessory includes a catheter with a hollow tube having at its distal end a remotely steerable head including a tubular receptacle directed axially and defining an interior volume capable of accommodating the capsule at least in the proximal portion thereof. The explantation accessory further includes a lasso including a flexible wire extending along the catheter and forming at its distal end a deformable loop emerging from the catheter. The lasso loop extends between two ends configured on two opposite ends of the hollow catheter tube, at least one of these loop ends being mobile relative to the catheter so as to allow tightening of the loop under the effect of a traction exerted proximally on the flexible wire along the catheter, and vice versa.

In a manner which is characteristic of one exemplary embodiment of the invention, the free end edge of the tubular container includes a protruding front portion, a rear portion in axial recess relative to the front portion and located diametrically opposite to the protruding front portion, and two bevel edges connecting the protruding front portion to the recessed rear portion.

According to various advantageous subsidiary characteristics:

The protruding front portion angularly extends over a sector of at least 90°;

One of the ends of the lasso loop is a fixed end integral with one of the bevel edges of the tubular receptacle and the other end of the lasso loop is a mobile end located on the flange in the opposite bevel;

The ends of the lasso loop are both mobile ends, respectively located on oppositely beveled edges;

In the latter case, the distance between, on the one hand, the location on the edge bevel of the fixed and/or mobile end of the lasso loop and, on the other hand, the rear recessed portion, is between 20 and 40% of the length of the tubular body of the capsule, and/or is between 5 and 20 mm for the explantation of a capsule, the length of the tubular body of which is 35 mm;

The location on the beveled edge of the fixed and/or mobile end of the lasso loop is located at a distance between 40 and 60% of the distance between the opposite ends of the front portion and of the recessed protruding portion;

The maximum length of the loop in expanded configuration is between 3 and 40 mm; for explantation of a capsule, the diameter of the tubular body is 6.5 mm;

The distal end of the protruding front portion carries a radiopaque marker;

The accessory further includes a telescopically mobile sub-catheter in the tube of the remotely steerable catheter and provided at its distal end with means for securing in rotation and in translation to the capsule in the proximal region thereof.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

A non-limitative exemplary embodiment of the invention will now be described.

Figure 1:
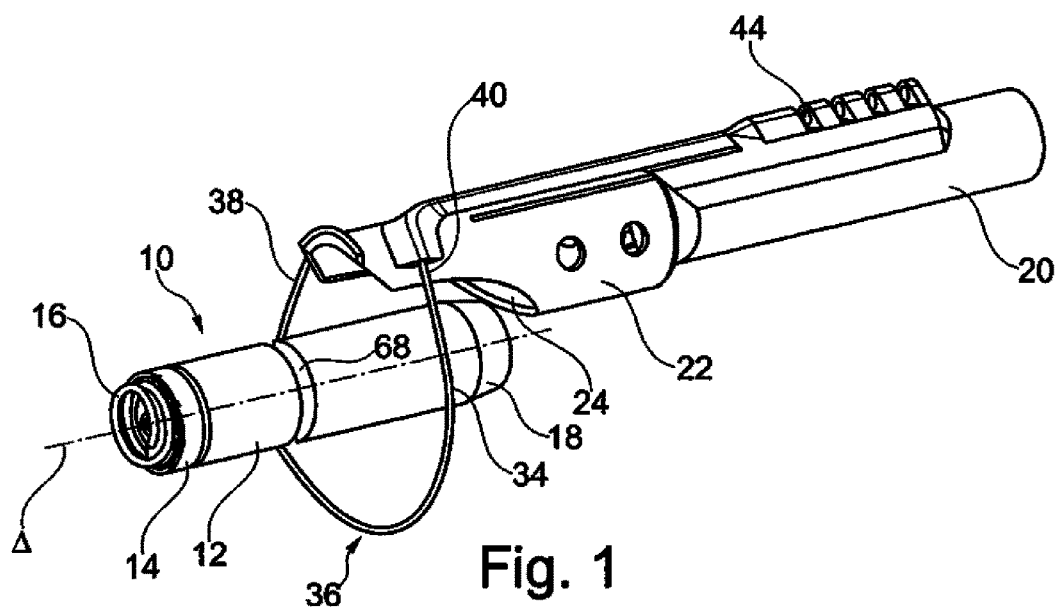
FIG. 1 is a perspective view of the distal end of the explantation accessory according to one embodiment of the invention with the capturing lasso loop surrounding the capsule to explant, at the beginning of the maneuver before tightening the loop.
Figure 5:
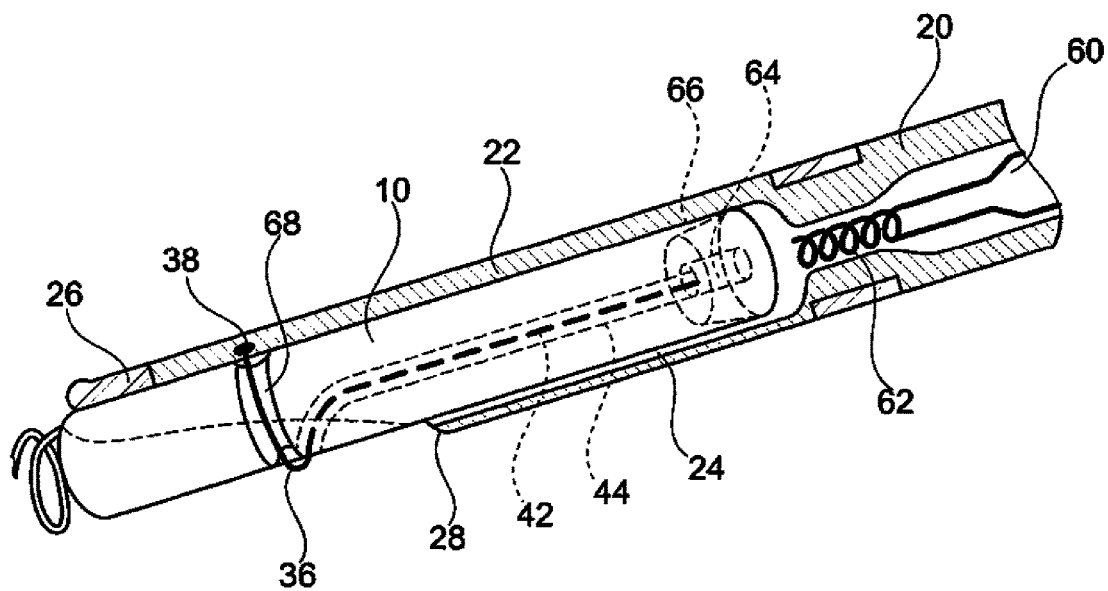
FIG. 5 is a partial section view of the receptacle of the explantation accessory according to one embodiment of the invention with the capsule retained therein by the loop of the lasso, the assembly being shown in the sub-catheter approach phase allowing the unscrewing of the capsule after coupling to the latter.
Figure 6:
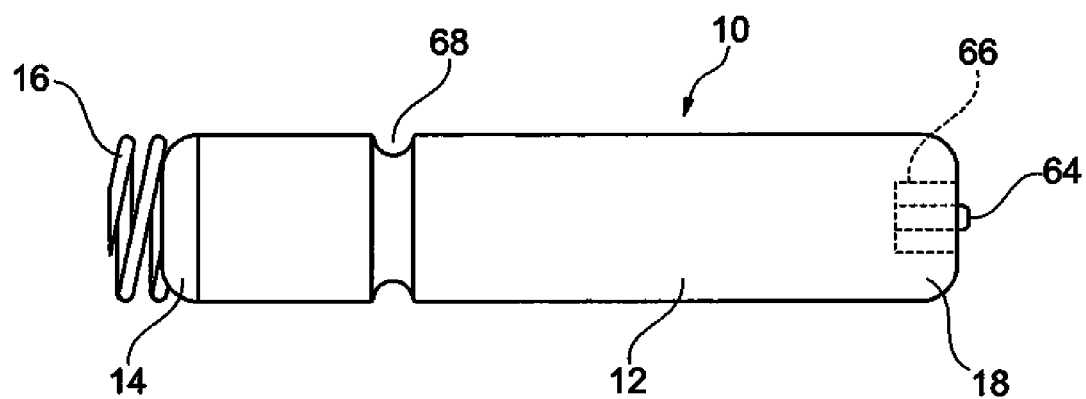
FIG. 6 is a view in elevation of a capsule, considered in isolation, showing the tubular body having a retaining groove for the lasso loop.

A leadless capsule 10, illustrated in FIGS. 1, 5 and 6, includes a cylindrical tubular body 12 having longitudinal axis Δ, enclosing the various electronic and power supply circuits of the capsule. Typical dimensions of such a capsule are a diameter of about 6.5 mm and a length of about 35 mm. At its distal end 14, the capsule 10 includes an anchoring helical screw 16 for fixing the capsule into the tissue, for example against a wall of a heart chamber after screwing during implantation. This screw can optionally be an active, electrically conductive screw for collecting cardiac depolarization potentials and/or the application of stimulation pulses. The proximal region 18 of the capsule 10 preferably has a rounded, atraumatic end and it is provided with a coupling member to an implantation or explantation sub-catheter, which will be described below with reference to FIGS. 5 and 6.

The explantation accessory of the invention includes a remotely steerable catheter, which is an accessory in itself known and entirely conventional, including a catheter tube manipulated from its proximal end by an operating handle (shown in FIG. 4) available to the practitioner, who can create and adjust a curvature in the distal region of the catheter to guide the end of it towards the intervention site.

In a manner characteristic of the invention, as illustrated in the figures, the catheter tube 20 is provided at its distal end a tubular receptacle 22 directed axially along the catheter tube and defining an interior volume 24 whose conformation and dimensions enable it to house all or part of the capsule, at least in the proximal region 18 thereof.

The free end edge of the tubular receptacle 22 is beveled, that is to say, more specifically, it includes a protruding front portion 26 and, diametrically opposed, a posterior portion 28 axially recessed relative to the front portion 26. The two prominent anterior 26 and posterior 28 portions are connected by two sloping edges 30, 32 forming the beveled shape of the end edge of the receptacle 22.

Figure 3:
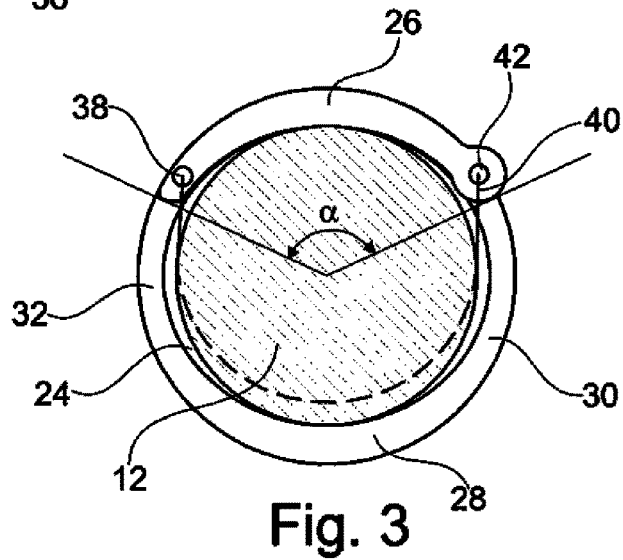
FIG. 3 is a front view of the receptacle member illustrated in FIG. 2, with a section through a capsule tightened by the lasso loop.

As illustrated in the front view of FIG. 3, the protruding front portion 26 angularly covers a sector forming an angle α of at least 90°, to enable it to provide a guiding function of the capsule during the introduction thereof into the interior volume 24.

Figure 2:
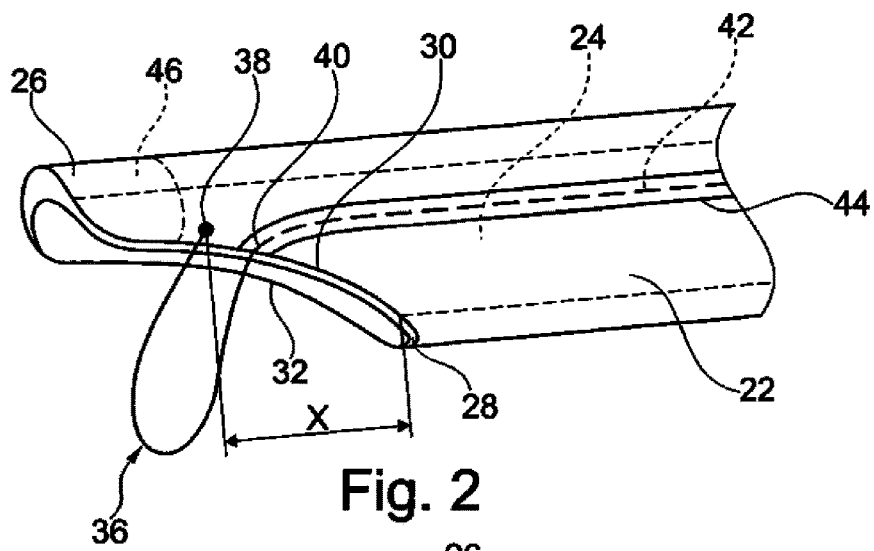
FIG. 2 is a detail view of the distal portion of the receptacle of an explantation accessory, with a capturing lasso loop.

The material of the receptacle 22 is chosen to be sufficiently flexible for not being traumatic against surrounding tissue during the explantation operation. It may for example be a thermoplastic elastomer such as PEBA (ether-amide block copolymer), a LDPE (low density polyethylene) or polyurethane. In addition, the material of the tubular receptacle 22 is advantageously loaded, in the protruding anterior region (region 46 in FIG. 2), of a radiopaque material improving the visibility of the accessory in this critical region during the approach procedure of the capsule by the tubular receptacle. This radiopaque material may be for example $BaSO_4$, or $TiO_2$.

The explantation accessory is further provided with a lasso capture system including a wire 34 deployable so as to form a loop 36 whose ends 38, 40 are located in the beveled end edge region of the tubular receptacle 22.

In the illustrated embodiment, one end 38 of the loop 36 is a fixed end, secured to the beveled edge 32 for example by overmolding, gluing or welding to a metallic insert incorporated in the tubular receptacle 22 at this location. The opposite end 40 of the loop 36 is, however, a mobile end, the wire 34 forming the loop extending in 42 along the tubular receptacle 22 and the catheter to the operating handle (shown in FIG. 4), the wire being guided in an eccentric lateral lumen 44 of the catheter over the entire length thereof.

The loop perimeter can thus typically vary, in the described embodiment, from 3 to 40 mm.

The wire 34, 42 of the capture lasso is advantageously a microcable of a shape memory alloy such as nitinol, allowing the lasso to keep a round shape loop and a direction perpendicular to the catheter axis once the loop is deployed. It is also possible to use a material such as a MP35N alloy or a steel containing a radiopaque material (e.g., a platinum-iridium alloy) so that the lasso loop can be visualized under fluoroscopy coupled to X-ray equipment.

Alternatively, both ends 38 and 40 of the loop 36 can be mobile ends, the wire then extending from the end 38 along the catheter, being guided in a second eccentric lateral lumen to the proximal end of the catheter and the operating handle of the accessory.

The positions of the ends 38, 40 of the loop 36 (fixed point or outlet of the eccentric lateral lumen 44) lie approximately in the middle of the respective beveled edges 30, 32, that is to say halfway between the ends of the anterior portion 26 and the posterior portion 28.

The distance (shown as X in FIG. 2) separating, in the axial direction, the positions of ends 38, 40 of the recessed posterior portion 28 is about 20 to 40% of the length of the tubular body 12 of the capsule, and/or has a length of between 5 and 20 mm for a capsule, whose length of the tubular body is 35 mm.

From the free state of the loop, wherein it is fully extended (configuration illustrated in FIG. 1), if one exerts from the proximal end of the catheter a pull on the wire 34 in the proximal direction 42, the end 40 of the loop will be gradually drawn into the lateral lumen 44 of the catheter, resulting in a gradual decrease in the perimeter of the loop 36 providing the sought "lasso" effect to capture the capsule 10. The maneuver is of course reversible to allow release or loosening of the loop and a repositioning of the lasso.

Figure 4:
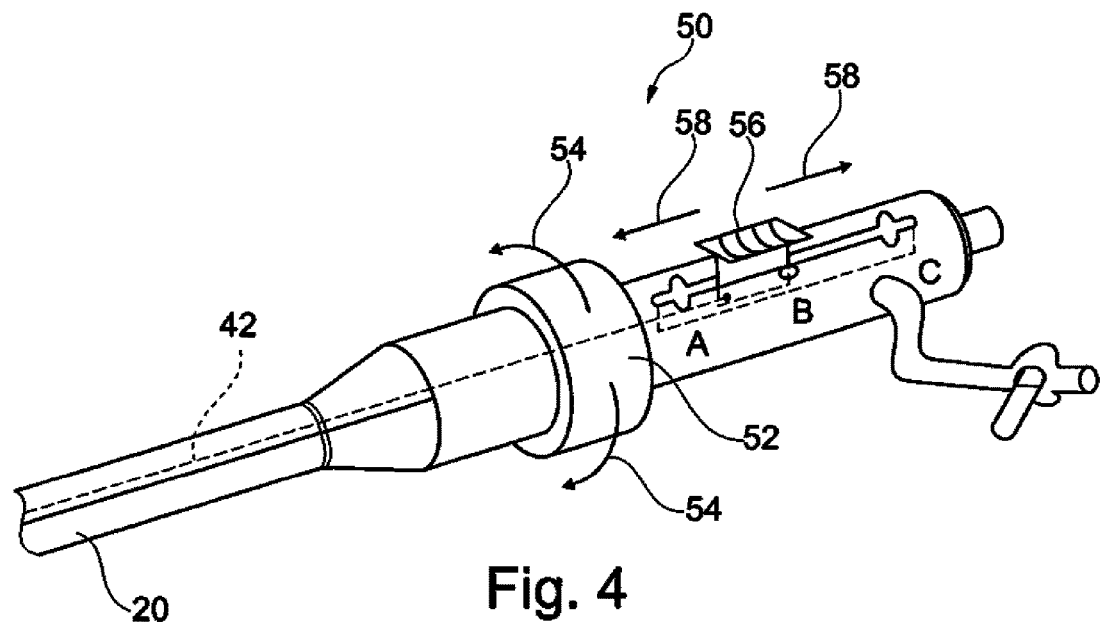
FIG. 4 shows the operating handle of an explantation accessory, located at the proximal end of the accessory and through which the practitioner controls the entire maneuver.

In FIG. 4, an example of the operating handle 50 of the explantation accessory of the invention is shown, this handle being situated at the proximal end of the catheter tube 20. The handle 50 includes, in a manner in itself known, a device 52 for maneuvering the steerable head of the catheter (the maneuverability illustrated by arrows 54), according to a mechanism itself known that is not described.

The operating handle is also provided with a slider 56 axially mobile between several positions (illustrated by arrows 58), this slider being connected to the microcable forming the control wire 42 of the lasso. The displacement of the wire in the axial direction controls the deployment or closes the capture loop 36 at the distal, opposite end of the catheter tube. These positions are indexed so as to be easily identified by the practitioner, for example with:

position A corresponding to a maximum loop perimeter, used during the search and capture phase of the capsule,
position B corresponding to a perimeter substantially equal to the loop circumference of the capsule, so as to permit a clamping-free slide of the loop axially along the body of the capsule, and
position C corresponding to the minimum loop perimeter, to ensure a clamping of the body of the capsule by this loop.

As shown in FIG. 5, the explantation accessory of the present disclosure allows the introduction into the inner lumen of the catheter tube 20, of a sub-catheter 60 ended at its distal end by a member 62 capable of coupling to the proximal portion of the capsule 10 after the latter has been completely introduced into the tubular receptacle 22, so as to allow a fastening in rotation and in translation with the latter.

The coupling member of the sub-catheter 60 in the capsule 10 can be realized in particular as described in the US patent application publication US20140378991 which describes a mechanism including a helix spring (here referenced 62) used in radial compression. The helix spring 62 is used for its constriction effect (an effect resulting from the increase of the inner diameter of the helix), and not for its properties of elasticity in axial traction/compression (an effect resulting from the distance extension or decrease of the spring coils). The helix spring 62 can be docked with an axial rod 64 formed in the proximal portion of the capsule within a housing 66 (shown in FIGS. 5 and 6). Once the spring 62 is pushed on the rod 64, the sub-catheter 60 and the capsule 10 are made integral in rotation, allowing an easy unscrewing of the capsule 10 from the opposite, proximal end of sub-catheter 60 by a simple rotation imparted to it.

Figure 7:
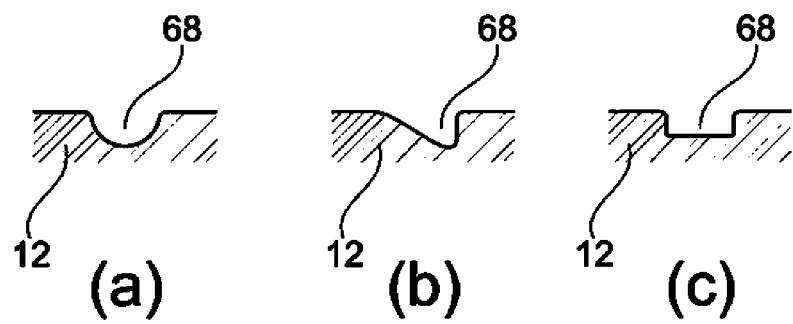
FIG. 7 illustrates different possible retaining groove profiles for the capsule illustrated in FIG. 6.

Advantageously, as illustrated in particular in FIGS. 5 to 7, the tubular body 12 of the capsule 10 is provided with an annular groove 68. The groove 68 has the function of improving the retaining of the capsule 10 into the tubular receptacle 22, and therefore the attachment of these two elements by avoiding any relative sliding. The groove 68 is formed on the tubular body at a level such that, as shown in FIG. 5, once the capsule 10 has been fully inserted into the tubular receptacle 22, the groove 68 is located axially at the ends 38, 40 of the loop 36 of the lasso.

FIG. 7 illustrates different possible configurations (a), (b) and (c) of the groove profile 68, to optimize the retention of the capsule by the wire of the lasso loop. The depth of the groove 68 is typically between 0.15 and 0.4 mm.

Figure 8:
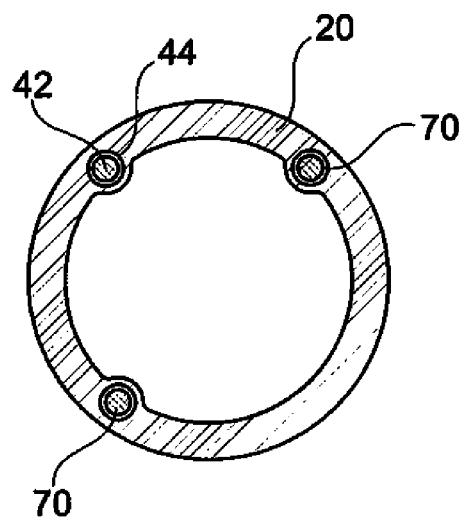
FIG. 8 is a cross-section view of the catheter, showing the two channels for the remotely steerable cables of the catheter and the channel for the clamping cable of the lasso.

FIG. 8 illustrates a cross section of the catheter, showing the two eccentric lateral lumens that allow the catheter being steerable, with the corresponding control wires 70, and the channel 44 in which the wire 42 for controlling the capture loop 36 slides.

Figure 9:
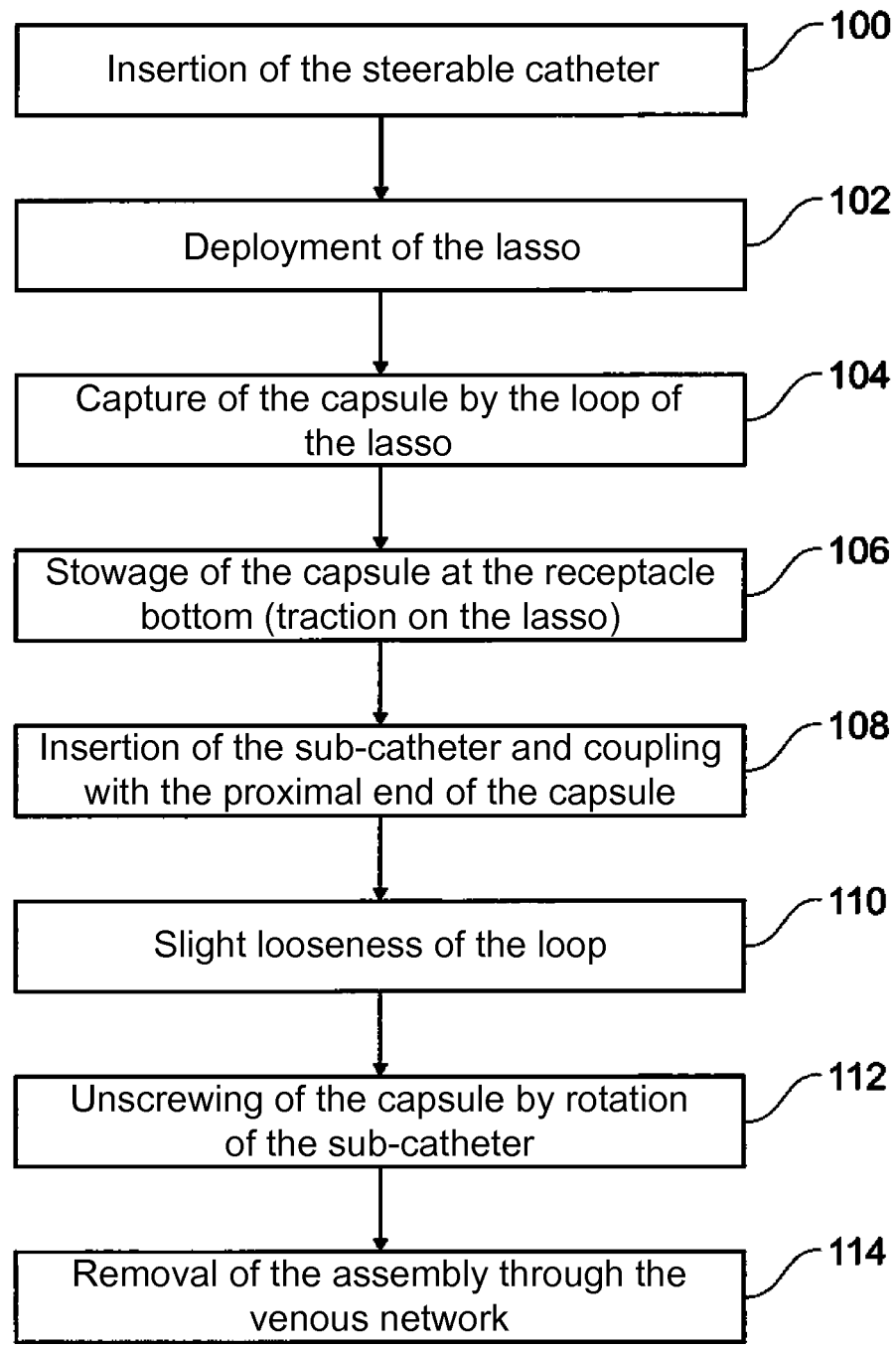
FIG. 9 is a flow chart detailing the different steps of the surgical explantation method of the capsule using the accessory according to one embodiment of the invention.

With reference to FIG. 9, the various steps of the explantation procedure of the capsule, through the accessory which is described above, will now be described.

The initial step (step 100) includes inserting into the venous system the steerable catheter and guiding the tubular receptacle 22 to a position close to the capsule to be extracted.

The loop of the lasso is then deployed (step 102) to come and surround the body of the capsule.

The loop of the lasso is then gradually closed (step 104), so as to bring the capsule close to the tubular receptacle 22 in a coaxial configuration.

The capsule is then secured to the bottom of the receptacle 22 by pulling on the loop of the lasso (step 106), which has the effect, taking into account the geometry of the different elements, to exert axial traction of the capsule allowing the latter to sink into the receptacle 22 until it comes into abutment with the bottom thereof.

The sub-catheter 60 may then be introduced (step 108) until the end spring 62 comes to coupling with the rod 64 of the capsule. The latter is firmly retained within the tubular receptacle 22 during the coupling operation, due to the complete closure of the loop 36 and due to the traction exerted on the cable 42 of the lasso, which has the effect of preventing any mechanical solicitation which would tend to push the capsule out of the receptacle.

The loop of the lasso is then slightly relaxed (step 110) so as to unscrew the capsule (step 112), the unscrewing being allowed by the coupling in rotation and in translation of the sub-catheter 60 with the capsule 10 by the spring 62 and of the rod 64.

The assembly formed by the explantation accessory and the capsule can then be gradually removed via the venous system (step 114), without any risk of tearing or damage to the surrounding tissue.

What is claimed is:

1. An explantation accessory for an intracorporeal capsule comprising a tubular body provided at its distal end with an anchoring screw member adapted to penetrate into tissue of a wall of an organ of a patient, the explantation accessory comprising:
    a catheter comprising a hollow tube carrying at its distal end a steerable head comprising a tubular receptacle directed axially and defining an interior volume suitable for housing the capsule at least in the proximal part thereof; and
    a lasso comprising a flexible wire extending along the catheter and forming at its distal end a deformable loop emerging from the catheter, the loop extending between two ends configured on two opposite ends of the catheter hollow tube, at least one of these ends of the loop being mobile relative to the catheter so as to allow tightening of the loop under the effect of a traction exerted on the flexible wire proximally along the catheter, and vice versa, wherein the loop is structured to engage a corresponding portion of the tubular receptacle of the catheter;
    wherein a free end of the tubular receptacle comprises:
        a protruding anterior portion;
        an axially recessed posterior portion with respect to the anterior portion and located diametrically opposite to the protruding anterior portion; and
        two beveled edges connecting the protruding anterior portion to the recessed posterior portion,
    wherein a first end of the loop extends from approximately a middle portion of the first beveled edge along a length of the first beveled edge and a second end of the loop extends from approximately a middle portion of the second beveled edge along a length of the second beveled edge, such that the loop extends across an opening of the tubular receptacle.

2. The explantation accessory of claim 1, wherein the protruding anterior portion extends angularly over a sector transverse to a longitudinal axis of the catheter of at least 90°.

3. The explantation accessory of claim 1, wherein one end of the loop of the lasso is a fixed end integral with one of the bevel edges of the tubular receptacle, and the other end of the loop of the lasso is a mobile end located on the opposite beveled edge.

4. The explantation accessory of claim 1, wherein the ends of the lasso loop are both mobile ends, respectively located on opposite beveled edges.

5. The explantation accessory of claim 1, wherein a distance between the mobile end of the loop of the lasso and the recessed posterior portion of the tubular receptacle is between 5 mm and 20 mm.

6. The explantation accessory of claim 1, wherein a length of the loop between the mobile end and a free end of the loop is between 3 mm and 40 mm.

7. The explantation accessory of claim 1, wherein a distal end of the protruding anterior portion carries a radiopaque marker.

8. The explantation accessory of claim 1, further comprising a sub-catheter telescopically mobile within the steerable head of the hollow tube of the catheter and provided at its distal end with means for securing in rotation and in translation the capsule in the proximal region thereof.

* * * * *